(12) United States Patent
Okazaki et al.

(10) Patent No.: US 11,296,731 B2
(45) Date of Patent: Apr. 5, 2022

(54) COMMUNICATION DEVICE

(71) Applicant: PHC Holdings Corporation, Tokyo (JP)

(72) Inventors: Makoto Okazaki, Ehime (JP); Seiitirou Iketani, Ehime (JP)

(73) Assignee: PHC HOLDINGS CORPORATION, Tokyo (JP)

( * ) Notice: Subject to any disclaimer, the term of this patent is extended or adjusted under 35 U.S.C. 154(b) by 34 days.

(21) Appl. No.: 16/769,384

(22) PCT Filed: Jan. 24, 2019

(86) PCT No.: PCT/JP2019/002322
§ 371 (c)(1),
(2) Date: Jun. 3, 2020

(87) PCT Pub. No.: WO2019/171807
PCT Pub. Date: Sep. 12, 2019

(65) Prior Publication Data
US 2021/0152196 A1    May 20, 2021

(30) Foreign Application Priority Data

Mar. 7, 2018    (JP) .............................. JP2018-040622

(51) Int. Cl.
*H04B 1/03*        (2006.01)
*H01Q 1/22*        (2006.01)
(Continued)

(52) U.S. Cl.
CPC .......... *H04B 1/0343* (2013.01); *H01Q 1/2208* (2013.01); *H01Q 1/273* (2013.01); *H01Q 1/38* (2013.01); *H01Q 1/427* (2013.01)

(58) Field of Classification Search
CPC .......... H04B 1/03; H04B 1/0343; H01Q 1/22; H01Q 1/2208; H01Q 1/273; H01Q 1/36; H01Q 1/38; H01Q 1/42; H01Q 1/427
See application file for complete search history.

(56) References Cited

U.S. PATENT DOCUMENTS

| 5,946,610 A | 8/1999 | Hama |
| 6,373,439 B1 | 4/2002 | Zürcher et al. |

(Continued)

FOREIGN PATENT DOCUMENTS

| CN | 1128441 | 8/1996 |
| CN | 1292583 | 4/2001 |

(Continued)

OTHER PUBLICATIONS

Extended European Search Report dated Apr. 9, 2021 in European Application No. 19763626.9.

(Continued)

*Primary Examiner* — Blane J Jackson
(74) *Attorney, Agent, or Firm* — Wenderoth, Lind & Ponack, L.L.P.

(57) ABSTRACT

A transmitter comprises a main body case, a controller that is provided inside the main body case, a communication unit that is connected to the controller, and an elongated antenna unit that is connected to the communication unit. The antenna unit is disposed along an inner wall surface of the main body case.

13 Claims, 8 Drawing Sheets

(51) Int. Cl.
  *H01Q 1/38* (2006.01)
  *H04B 1/034* (2006.01)
  *H01Q 1/27* (2006.01)
  *H01Q 1/42* (2006.01)

(56) References Cited

U.S. PATENT DOCUMENTS

| | | | |
|---|---|---|---|
| 6,914,564 B2 | 7/2005 | Barras et al. | |
| 8,348,835 B2 | 1/2013 | Fujimori | |
| 9,011,332 B2 * | 4/2015 | Heller | A61B 5/0031 |
| | | | 600/365 |
| 9,184,490 B2 * | 11/2015 | Crouther | A61M 5/172 |
| 9,409,018 B2 | 8/2016 | Tourrel et al. | |
| 10,232,185 B2 | 3/2019 | Tourrel et al. | |
| 11,103,185 B2 * | 8/2021 | Denda | A61B 5/1455 |
| 2004/0145975 A1 | 7/2004 | Barras et al. | |
| 2004/0155818 A1 | 8/2004 | Barras et al. | |
| 2006/0264083 A1 | 11/2006 | Fujimori | |
| 2007/0041275 A1 | 2/2007 | Barras et al. | |
| 2008/0143619 A1 | 6/2008 | Wotherspoon | |
| 2010/0198034 A1 * | 8/2010 | Thomas | A61B 5/0022 |
| | | | 600/365 |
| 2010/0321272 A1 | 12/2010 | Yukimoto et al. | |
| 2011/0006953 A1 | 1/2011 | Chiang et al. | |
| 2011/0121822 A1 * | 5/2011 | Parsche | H01Q 7/00 |
| | | | 324/157 |
| 2011/0288574 A1 | 11/2011 | Curry et al. | |
| 2011/0319729 A1 | 12/2011 | Donnay et al. | |
| 2012/0010642 A1 | 1/2012 | Lee et al. | |
| 2012/0190941 A1 | 7/2012 | Donnay et al. | |
| 2012/0190942 A1 | 7/2012 | Donnay et al. | |
| 2012/0190943 A1 | 7/2012 | Donnay et al. | |
| 2012/0190951 A1 | 7/2012 | Curry et al. | |
| 2012/0197098 A1 | 8/2012 | Donnay et al. | |
| 2012/0197222 A1 | 8/2012 | Donnay et al. | |
| 2015/0025338 A1 | 1/2015 | Lee et al. | |
| 2015/0088226 A1 | 3/2015 | Tourrel et al. | |
| 2016/0030078 A1 | 2/2016 | Lee et al. | |
| 2016/0128615 A1 | 5/2016 | Curry et al. | |
| 2016/0165719 A1 * | 6/2016 | Li | A61B 5/6823 |
| | | | 361/749 |
| 2016/0171363 A1 * | 6/2016 | Mei | A61B 5/0008 |
| | | | 235/492 |
| 2016/0310737 A1 | 10/2016 | Tourrel et al. | |
| 2017/0001483 A1 | 1/2017 | Sabatini et al. | |
| 2017/0020456 A1 * | 1/2017 | Pace | A61B 5/6833 |
| 2018/0048056 A1 * | 2/2018 | Jow | H01Q 1/38 |
| 2019/0076073 A1 | 3/2019 | Donnay et al. | |
| 2019/0298240 A1 | 10/2019 | Lee et al. | |
| 2020/0069190 A1 * | 3/2020 | Ryu | A61B 5/0008 |

FOREIGN PATENT DOCUMENTS

| | | |
|---|---|---|
| CN | 1524317 | 8/2004 |
| CN | 101878561 | 11/2010 |
| CN | 101958456 | 1/2011 |
| CN | 102015374 | 4/2011 |
| CN | 102307517 | 1/2012 |
| CN | 104511091 | 4/2015 |
| CN | 106163835 | 11/2016 |
| EP | 1 448 041 | 8/2004 |
| JP | 2003-210395 | 7/2003 |
| JP | 2008-48402 | 2/2008 |
| JP | 5044695 | 10/2012 |
| JP | 2013-523217 | 6/2013 |
| JP | 2013-247599 | 12/2013 |
| KR | 10-2013-0137427 | 12/2013 |
| WO | 2011/162843 | 12/2011 |

OTHER PUBLICATIONS

Office Action dated Jun. 11, 2021 in corresponding Chinese Patent Application No. 201980006601.4, with partial English translation.
International Search Report dated Apr. 9, 2019 in International (PCT) Application No. PCT/JP2019/002322.
Office Action dated Oct. 13, 2021 in corresponding Chinese Patent Application No. 201980006601.4, with partial English translation.
Notice of Allowance dated Dec. 28, 2021 in Chinese Application No. 201980006601.4 with English translation thereof.

* cited by examiner

COMMUNICATION DEVICE

TECHNICAL FIELD

The present application relates to a communication device that performs communication using an antenna unit.

BACKGROUND ART

The configuration of a conventional communication device is as follows.

A conventional communication device had a configuration comprising a main body case, a controller provided in the main body case, a communication unit connected to the controller, and an antenna unit connected to the communication unit, in which the antenna unit was used for communication with external devices.

Such a communication device is used, for example, in a biological information measuring device that continuously measures a blood glucose level, in which the measured blood glucose level is transmitted to a mobile telephone using a communication device (for example, Patent Literature 1 given below).

The biological information measuring device is worn on the patient's arm continuously for one to two weeks in order to continuously measure the blood glucose level. Since it is always worn on the patient's body, there is a need for a biological information measuring device that is as small as possible.

Therefore, the communication device, including the antenna unit, also needs to be made smaller.

CITATION LIST

Patent Literature

Patent Literature 1: Japanese Unexamined Patent Application Publication No. 2013-523217

SUMMARY

Technical Problem

A problem encountered with the above conventional example is that the communication device ends up being large.

Specifically, with a conventional communication device, the controller, the communication unit, and the antenna unit are all mounted on the same substrate.

The antenna unit may be adversely affected by any metal that may be nearby. For this reason, a special area is provided around the antenna unit where other components that contain metal (such as a control microprocessor, a communication IC, a battery, etc.) are not mounted. As a result, the size of the substrate is increased in proportion to the special area for isolating the antenna unit from other components containing metal, so the communication device ends up being larger.

In view of this, it is an object of the present invention to make a communication device including an antenna unit smaller than in the past.

Solution to Problem

In order to achieve this object, the communication device of the present invention comprises a main body case, a controller that is provided inside the main body case, a communication unit that is connected to the controller, and an elongated antenna unit that is connected to the communication unit. The antenna unit is disposed along an inner wall surface of the main body case.

This configuration achieves the stated object.

Advantageous Effects

In the present invention, the elongated antenna unit is disposed along an inner wall surface of the main body case.

Accordingly, the antenna unit is disposed at a position that is away from other components that contain metal, that is, along an inner wall surface. Therefore, the substrate on which other components containing metal are mounted does not have to be provided with an area around the antenna unit in which necessary components containing metal are not mounted, as opposed to the conventional practice.

As a result, the size of the substrate can be reduced, so the communication device can be more compact.

DESCRIPTION OF EMBODIMENTS

Embodiments of the present invention will now be described in detail with reference to the drawings.

In the following embodiments, "upper" and "lower" represent "upper" and "lower" in the usage state of the biological information measuring device 1 shown in FIG. 2 (the state of being attached to the patient's body 2).

Embodiment 1

Figure 1:
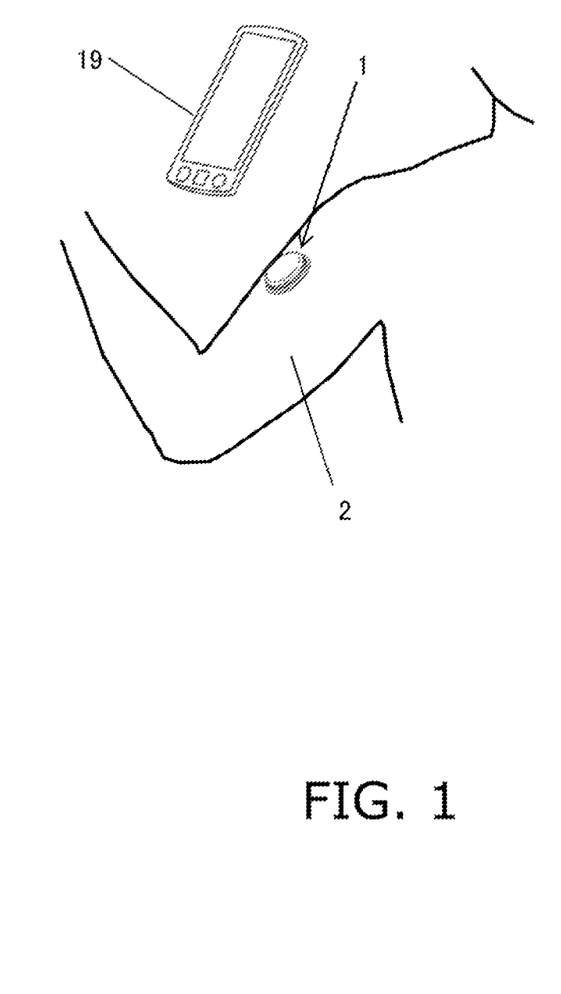
FIG. 1 is an oblique view of a biological information measuring device to which the transmitter according to Embodiment 1 of the present invention has been applied.

FIG. 1 shows a biological information measuring device 1 for performing continuous blood glucose measurement. As shown in FIG. 1, the biological information measuring device 1 continuously measures the blood glucose level every five minutes for one to two weeks while being attached to the upper arm 2 of the patient, for example. This makes it possible to ascertain tendencies in the patient's blood glucose state, and the blood glucose state when sleeping.

Figure 2:
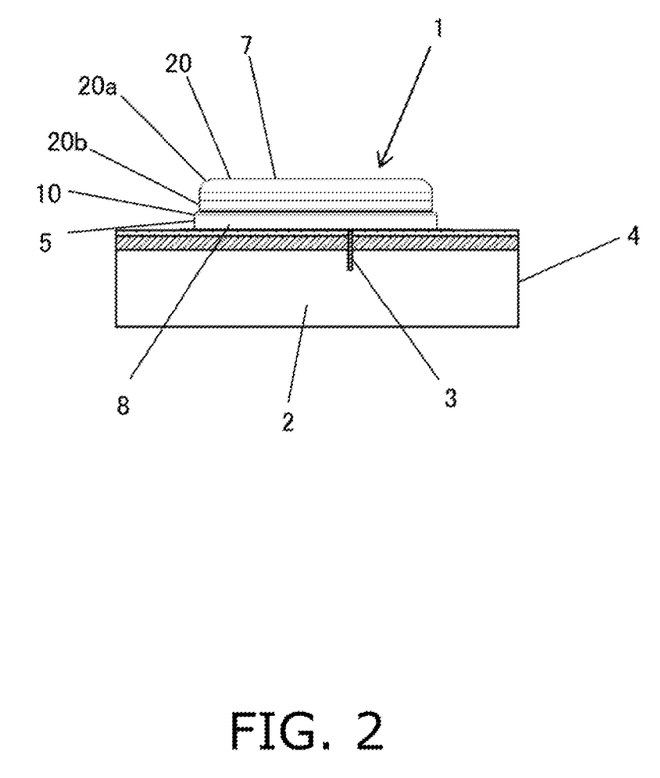
FIG. 2 is a diagram showing the mounted state of the biological information measuring device in FIG. 1.

FIG. 2 is a cross section of the biological information measuring device 1 in the state of FIG. 1.

As shown in FIG. 2, a needle-shaped sensor 3 protrudes from the lower surface of the biological information measuring device 1. The sensor 3 is left in an upper arm 2, in a state in which the tip has reached the skin tissue 4. This sensor 3 is used to continuously measure the concentration of glucose in the interstitial fluid (blood glucose level).

Figure 3:
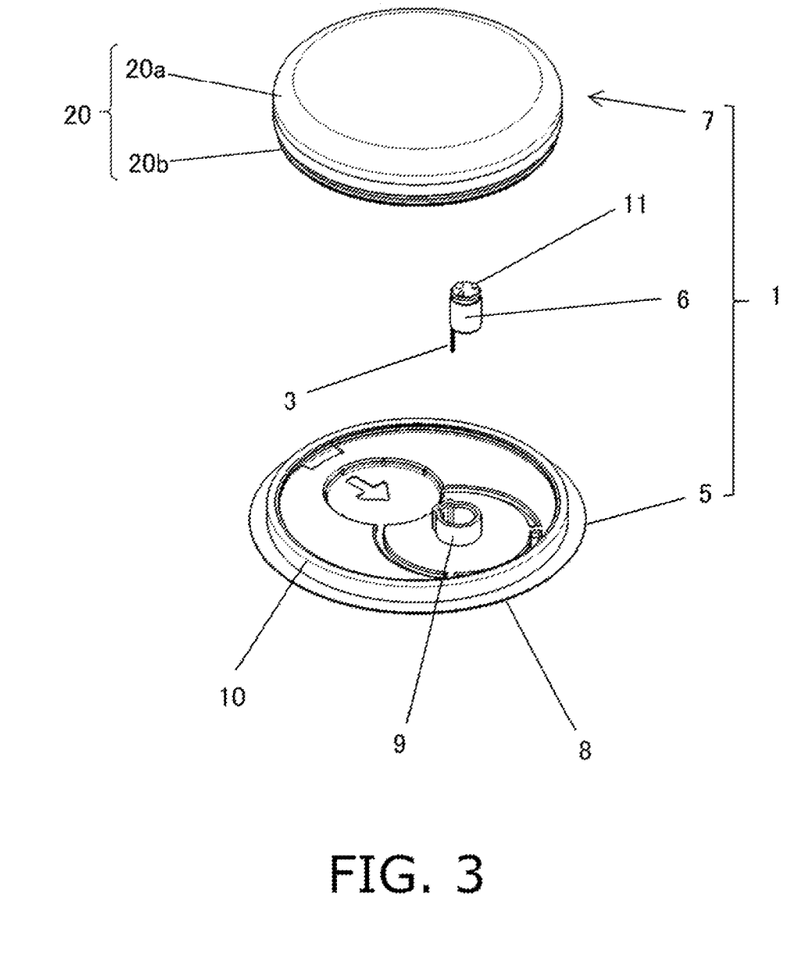
FIG. 3 is an exploded oblique view of the biological information measuring device in FIG. 1.

FIG. 3 shows a configuration of the biological information measuring device 1.

As shown in FIG. 3, the biological information measuring device 1 comprises a base unit 5, a sensor unit 6, and a transmitter 7 (an example of a communication device).

The base unit 5 is formed in a disk shape from a resin. An adhesive portion is provided on the lower surface of the base unit 5 to make it easy to attach to the patient's skin. A cylindrical sensor unit mounting portion 9 is provided near the center of the base unit 5. The sensor unit 6 is mounted on the sensor unit mounting portion 9.

The sensor 3 is attached to the sensor unit 6 such that the needle-shaped sensor 3 projects from the lower surface.

The transmitter 7 is formed in a dome shape from a resin. The configuration of the transmitter 7 will be described in detail below.

The mounting of the biological information measuring device 1 will now be described with reference to FIGS. 2 and 3.

First, the patient mounts the base unit 5 in FIG. 3 on the upper arm 2, with the adhesive portion 8 serving as the bonding surface.

Next, the patient uses a sensor mounting device (not shown) to mount the sensor unit 6 on the sensor unit mounting portion 9 of the base unit 5. Then, the sensor 3 punctures the upper arm 2, and is left in the upper arm 2 (see FIG. 2).

The lower portion of the transmitter 7 is then fitted into an annular fitting portion 10 of the base unit 5, at which point the mounting of the biological information measuring device 1 is complete. At this time, a connection terminal 11 of the sensor unit 6 is electrically connected to a measurement unit 12 (see FIG. 4) of the transmitter 7.

Figure 4:
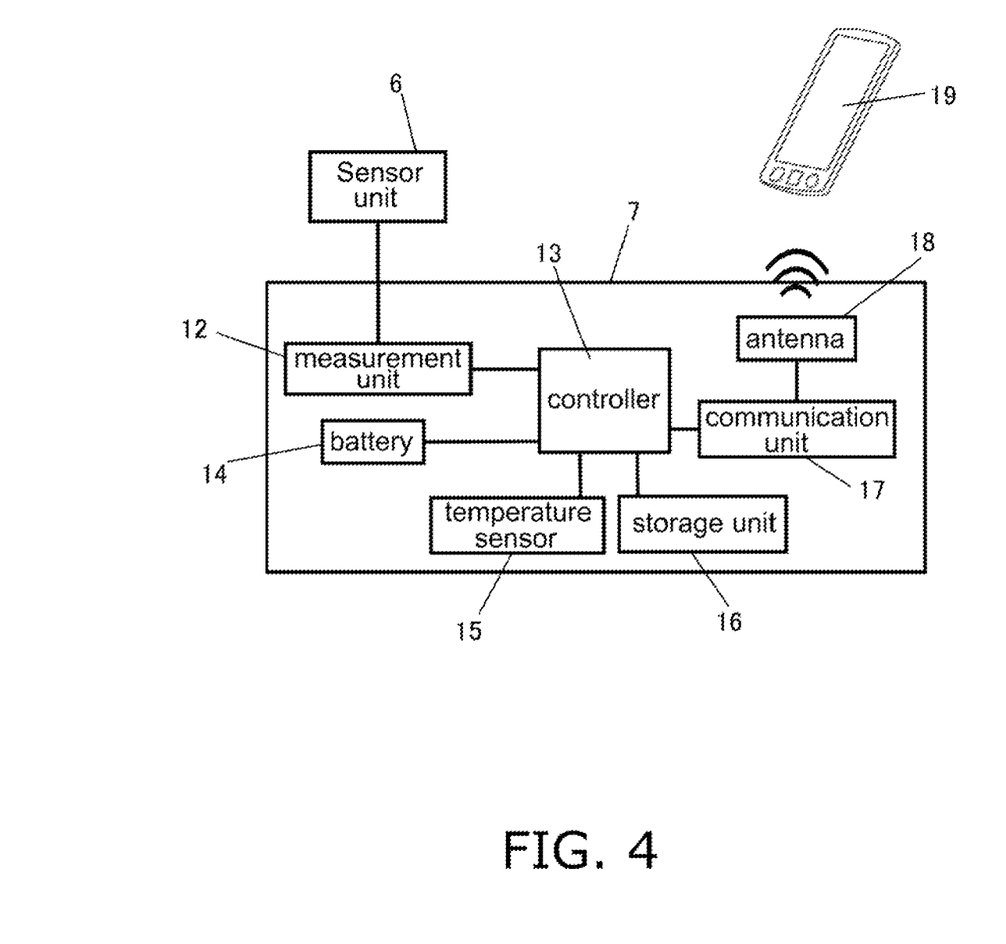
FIG. 4 is a control block diagram of the transmitter in FIG. 1.

FIG. 4 shows a control block diagram of the transmitter 7.

The measurement unit 12 to which the sensor unit 6 is connected is electrically connected to the controller 13. A battery 14, a temperature sensor 15, a storage unit 16, and a communication unit 17 are electrically connected to the controller 13. An antenna unit 18 is electrically connected to the communication unit 17.

The battery 14 is provided inside a main body case 20 and supplies power to the various units connected to the controller 13. More specifically, the battery 14 is disposed on a first substrate 22 that is attached to the bottom surface of a lower case 20b of the main body case 20 (see FIGS. 5 and 6).

With the biological information measuring device 1, the measurement unit 12 measures the blood glucose level using the sensor unit 6 at predetermined time intervals (such as every 5 minutes). The controller 13 corrects the blood glucose level on the basis of the temperature sensed by the temperature sensor 15, and stores the blood glucose value in the storage unit 16.

When the controller 13 operates the communication unit 17, the communication unit 17 transmits various kinds of information, including the measurement values stored in the storage unit 16, to an external device (such as a mobile telephone 19) via the antenna unit 18.

The basic configuration and operation in this embodiment are as described above.

The configuration of the transmitter 7 in this embodiment will now be described in detail.

The transmitter 7 occupies a large part of the biological information measuring device 1, as shown in FIG. 3. In this embodiment, the biological information measuring device 1 is made smaller by reducing the size of the transmitter 7.

Figure 5:
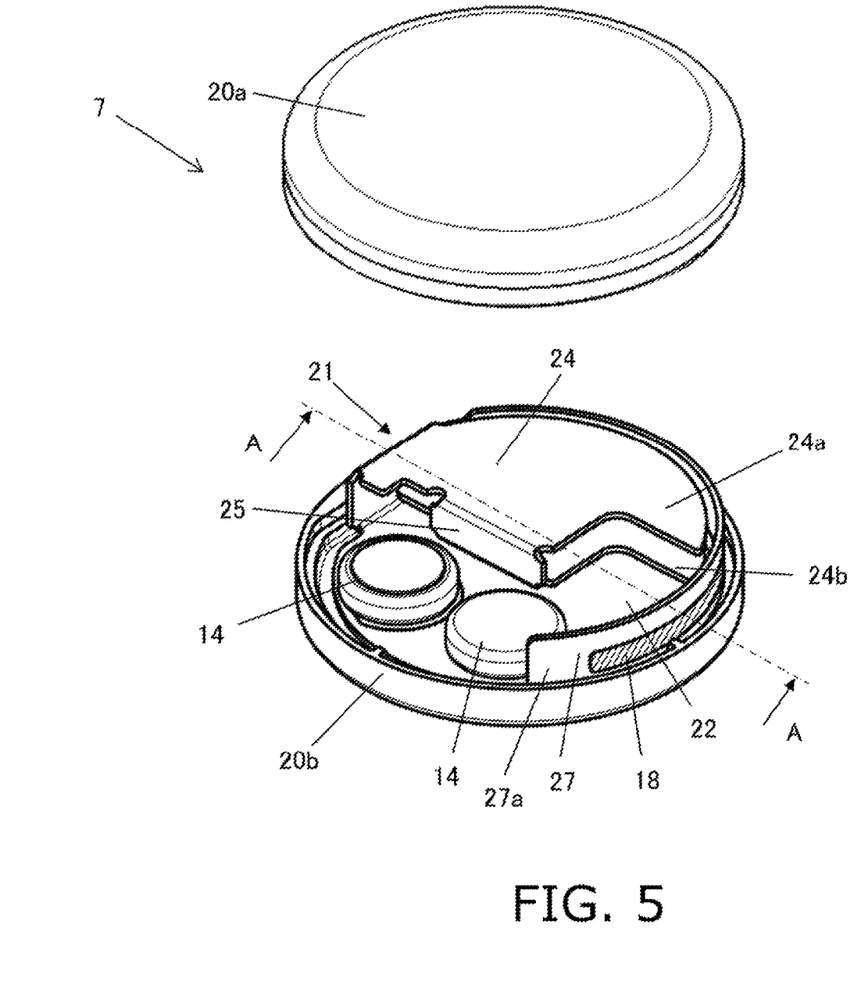
FIG. 5 is an exploded oblique view of the transmitter in FIG. 1.
Figure 6:
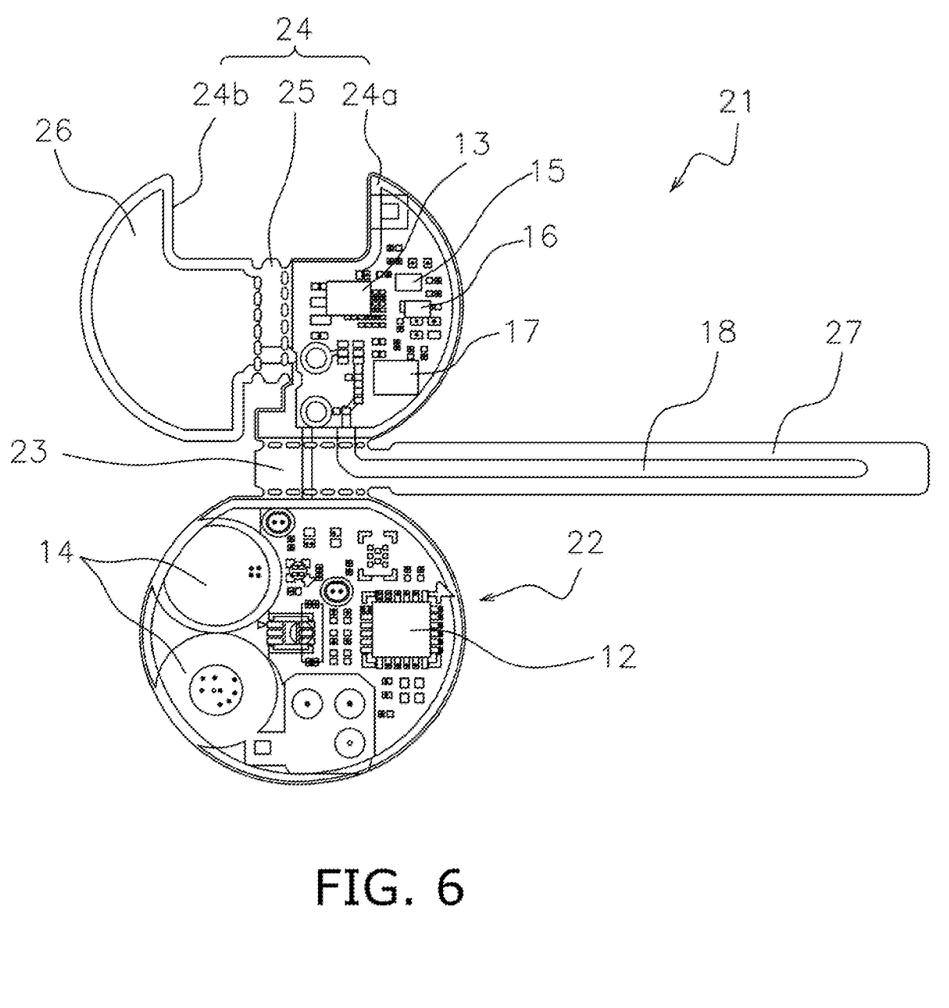
FIG. 6 is a front view of the control substrate in FIG. 5.

As shown in FIGS. 5 and 6, the transmitter 7 comprises a dome-shaped main body case 20 and a base substrate 21. The base substrate 21 has a circular first substrate 22, a connector 23, a circular second substrate 24, a linking unit 25, and an antenna unit 27 (see FIGS. 5 and 6).

Figure 8:
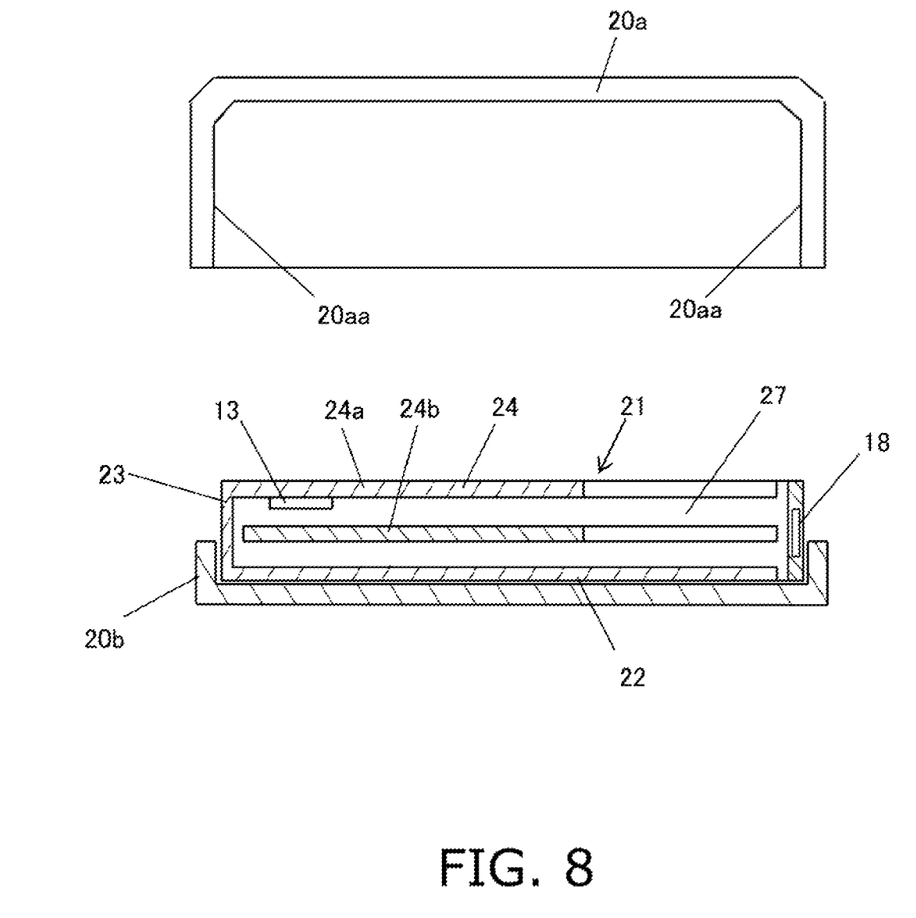
FIG. 8 is a cross section along the A-A line in FIG. 5.

The main body case 20 has a resin upper case 20a and a resin lower case 20b. The upper case 20a is formed in a dome shape having an opening on the lower surface side, and has an inner peripheral surface (inner wall surface) 20aa inside a cylindrical shape as shown in FIG. 8. The lower case 20b is formed in a cylindrical shape with a bottom, and the upper case 20a is attached so as to cover the upper part as shown in FIG. 5.

FIG. 5 shows the internal configuration of the transmitter 7, showing a state in which the upper case 20a has been removed. The base substrate 21 is disposed inside the lower case 20b.

FIG. 6 is a developed view of the base substrate 21 in FIG. 5.

As shown in FIG. 6, the base substrate 21 is configured to include a circular first substrate 22, a connector 23, and a circular second substrate 24.

The first substrate 22 is disposed substantially parallel to the bottom surface of the main body case 20 (the lower case 20b) (see FIG. 8). Also, on the first substrate 22, the measurement unit 12 is disposed on the first end side (the right side in FIG. 6), and two batteries 14 are disposed on the second end side, which is the opposite side (the left side in FIG. 6). That is, the first substrate 22 is an analog substrate on which analog components for performing measurement are disposed.

The connector 23 is formed in a rectangular shape, and links the first substrate 22 and the second substrate 24 on its long side. Also, as shown in FIGS. 7 and 8, the connector 23 is disposed in the gap between the first substrate 22 and the second substrate 24, which are disposed substantially in parallel with each other, so as to be substantially perpendicular the first substrate 22 and the second substrate 24.

Like the first substrate 22, the second substrate 24 is disposed substantially parallel to the bottom surface of the main body case 20 (the lower case 20b). As shown in FIG. 6, the second substrate 24 is configured to include a component substrate 24a provided on a first end side, a ground substrate 24b provided on a second end side (the opposite side), and a linking unit 25 that links these two substrates 24a and 24b.

Figure 7:
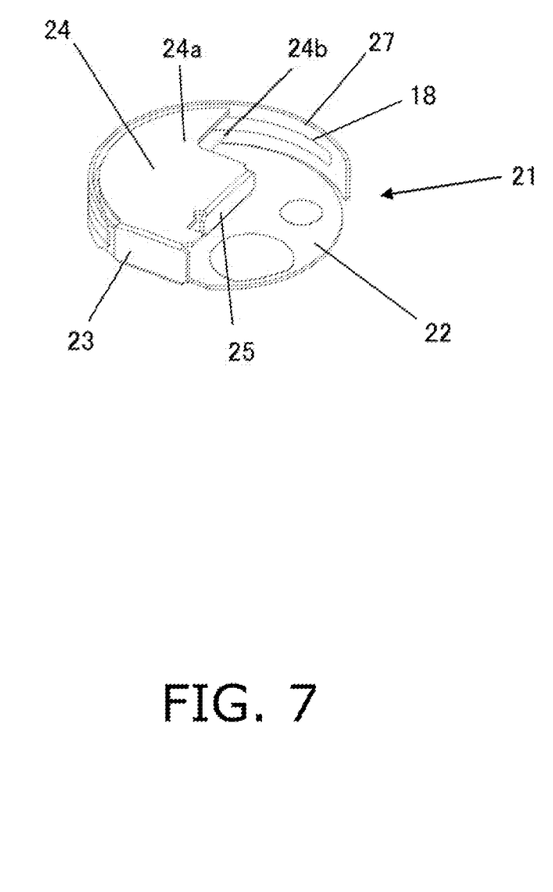
FIG. 7 is an oblique view in which the control substrate in FIG. 6 has been assembled.

As shown in FIG. 7, the component substrate 24a and the ground substrate 24h are folded around the rectangular linking unit 25, and are provided substantially parallel to each other with the linking unit 25 interposed therebetween. The component substrate 24a is linked to the first substrate 22 via the connector 23, Also, as shown in FIG. 6, the component substrate 24a and the ground substrate 24b are symmetrically disposed with the linking unit 25 interposed therebetween.

In the second substrate 24, the controller 13, the temperature sensor 15, the storage unit 16, and the communication unit 17 are disposed on the component substrate 24a. A ground 26 is disposed over substantially the entire surface on the ground substrate 24b. That is, the second substrate 24 is a digital substrate on which digital components such as the controller 13 and the temperature sensor 15 are disposed.

Thus, in the base substrate 21, the first substrate 22 (analog substrate) and the second substrate 24 (digital substrate) are linked at their respective ends by the connector 23, and are disposed substantially parallel to each other within the main body case 20 (see FIG. 8). An antenna substrate (third substrate) 27 is linked to a short side of this connector 23.

As shown in FIG. 6, the antenna substrate 27 has a rectangular shape, a first end side is linked to the connector 23, and a second end side on the opposite side from the first end side is a free end. The long antenna unit 18 is provided to the antenna substrate 27 from the first end side to the second end side.

The first substrate 22, the connector 23, the second substrate 24, and the antenna substrate 27 are constituted by flexible substrates that are linked to each other, and the electronic components disposed on the substrates 22, 24, and 27 are electrically connected.

The base substrate 21 is housed inside the main body case 20 in a state of being folded small.

More specifically, as shown in FIGS. 6 and 7, first, in the second substrate 24, the ground substrate 24b is folded so as to overlap the component substrate 24a, with the linking unit 25 at the center. The ground substrate 24b is disposed opposite the component substrate 24a with a gap corresponding to the width of the linking unit 25 therebetween.

Next, this folded second substrate 24 is folded so as to overlap the first substrate 22, with the connector 23 at the center. As shown in FIG. 7, the second substrate 24 is disposed opposite the first substrate 22 via the connector 23.

In the state shown in FIG. 7, the components mounted on the second substrate 24 and the components mounted on the first substrate 22 are disposed opposite each other. In view of this, in order to prevent the components mounted on these substrates from interfering with each other, a specific gap is formed, depending on the width of the connector 23 (the height in the vertical direction in the drawing), between the first substrate 22 and the second substrate 24. The rectangular antenna substrate 27 is wound along the outer peripheral portions of the first substrate 22 and the second substrate 24 so as to cover the outer peripheral portion of this gap.

Consequently, as shown in FIG. 8, the antenna substrate 27 is disposed substantially parallel to the inner peripheral surface (inner wall surface) 20aa of the upper case 20a of the main body case 20. As a result, the antenna unit 18 provided on the antenna substrate 27 is disposed inside the main body case 20, along the outermost peripheral side.

That is, in this embodiment, the long antenna unit 18 disposed on the antenna substrate 27 is disposed along the inner peripheral surface 20aa of the main body case 20.

Accordingly, the antenna unit 18 is disposed at a position that is away from other components containing metal with which there may be an adverse effect (such as the measurement unit 12, the controller 13, the battery 14, and the communication unit 17), that is, inside the main body case 20, along the inner wall surface on the outermost peripheral side. Therefore, with the configuration in this embodiment, the first substrate 22 or the second substrate 24 on which other components containing metal are mounted do not need to be provided with a special area around the antenna unit 18 where no components are mounted.

As a result, the base substrate 21 can be made smaller, so the transmitter 7, which is a communication device, can be made smaller than in the past.

In this embodiment, as shown in FIG. 7, the antenna substrate 27 is disposed so as to be wound along the outer peripheral portions of the first substrate 22 and the second substrate 24.

This means that the antenna unit 18 can be formed in the optimal length by taking advantage of the flat portion along the inner peripheral surface 20aa of the main body case 20 on the outer peripheral side of the first substrate 22 and the second substrate 24. As a result, communication through the antenna unit 18 will be more stable.

Also, a specific gap in the vertical direction is formed between the first substrate 22 and the second substrate 24, and more specifically, between the first substrate 22 and the component substrate 24a.

In this embodiment, this gap is utilized to dispose the antenna substrate 27 at a position corresponding to the gap.

Accordingly, since the antenna substrate 27 is disposed in the gap formed between the first substrate 22 and the second substrate 24 of the folded base substrate 21, the base substrate 21 can be made smaller. This also allows the transmitter 7 to be more compact than in the past.

Furthermore, in this embodiment, in order to make the transmitter 7 smaller than in the past, the first substrate 22, the connector 23, the second substrate 24, and the antenna substrate 27 are constituted by linked flexible substrates.

This allows the base substrate 21 to be folded. Also, the antenna substrate 27 can be bent and disposed in the space on the outer peripheral side of the folded base substrate 21, so as to follow along the outer peripheral portion of the base substrate 21.

As a result, the space in which the base substrate 21 is installed can be made smaller, so the transmitter 7 can be more compact than in the past.

Furthermore, in this embodiment, in order to stably dispose the folded base substrate 21 in the main body case 20, the antenna unit 18 is formed by a conductive pattern, and in the antenna substrate 27, the front and rear surfaces of the antenna unit 18 are laminated with a resin substrate.

Accordingly, the antenna substrate 27 tends to maintain a flat state due to the rigidity of the resin substrates.

That is, as shown in FIG. 5, the antenna substrate 27 is bent in an arc shape along inner peripheral surface 20aa of the main body case 20. The antenna substrate 27 attempts to return to its flat state due to the rigidity of the resin substrates attached to the front and rear surfaces, and is therefore pressed against the inner peripheral surface 20aa of the main body case 20 by this restoring force.

As a result, the antenna unit 18 is stably disposed within the main body case 20.

Also, as shown in FIG. 5, the battery 14 is disposed in the main body case 20. The battery 14 is a metal-containing component, as are the measurement unit 12, the controller 13, the communication unit 17, and so forth, and is a particularly large metal component, and therefore may have an adverse effect on the antenna unit 18.

In view of this, with the transmitter 7 in this embodiment, the battery 14 that supplies power to the controller 13 and the communication unit 17 is disposed inside the main body case 20, and the battery 14 is disposed at a position near the inner peripheral surface on the opposite side from the peripheral surface 20aa where the antenna unit 18 is disposed.

Accordingly, since the antenna unit 18 is disposed at a position away from the metal battery 14, the adverse effect of the battery 14 on the antenna unit 18 can be avoided, and communication can be more stable.

In this embodiment, the battery 14 is disposed on the first substrate 22, but the battery 14 may instead be disposed on the second substrate 24.

Also, the distal end of the antenna unit 18 provided on the antenna substrate 27 extends only to in front of a position close to the battery 14, as shown in FIG. 5. However, as shown in FIG. 5, the antenna substrate 27 has an extension (non-conducting portion) 27a that extends farther to the distal end side than the distal end of the antenna unit 18.

The extension 27a is a portion of the antenna substrate 27 through which electricity does not flow, and is extended to a portion where the gap between the outer peripheral surface of the battery 14 and the inner peripheral surface 20aa of the main body case 20 is at its narrowest.

That is, the antenna substrate 27 constituted by a flexible substrate starts out in a flat shape, but is itself curved along the inner peripheral surface of the main body case 20. Therefore, the distal end of the antenna substrate 27 extended to near the battery 14 is stably disposed in a state in which it is appropriately pressed against the inner peripheral surface 20aa of the main body case 20. This also stabilizes the characteristics of the antenna unit 18.

On the other hand, if the main body case 20 should be dropped or subjected to excessive vibration before being attached to the upper arm 2, there is the risk that the distal end of the antenna substrate 27 may inadvertently move within the main body case 20, and as a result the characteristics of the antenna unit 18 may change.

In view of this, in this embodiment, as described above, the antenna substrate 27 itself is further extended beyond the distal end of the antenna unit 18, as shown in FIG. 5. The extension 27a is extended to the portion where the gap between the outer peripheral surface of the battery 14 and the inner peripheral surface 20aa of the main body case 20 is at its narrowest.

As a result distal end portion 27a is disposed in the small gap between the outer peripheral surface of the battery 14 and the inner peripheral surface 20aa of the main body case 20, so the distal end of the antenna substrate 27 is less likely to be moved inadvertently due to the above-mentioned dropping or excessive vibration, and the characteristics of the antenna unit 18 can be maintained in an extremely stable state.

Furthermore, with the transmitter 7 in this embodiment, the first substrate 22 (analog substrate) and the second substrate 24 (digital substrate) are isolated via the connector 23 as described above. This prevents the electrical characteristics of the digital control circuit from adversely affecting the characteristics of the analog measurement circuit.

As described above, with the transmitter 7 in this embodiment, the base substrate 21 shown in FIG. 7 is folded in order to reduce the size of the transmitter 7 while minimizing adverse effects on the measurement.

In a folded state, the digital circuit of the component substrate 24a of the second substrate 24 is disposed opposite a position close to the analog circuit of the first substrate 22. Therefore, there is a risk that the electrical characteristics of the digital circuit may adversely affect the analog measurement circuit.

In view of this, in this embodiment, as shown in FIG. 7, in a state in Which the second substrate 24 is disposed opposite a position close to the first substrate 22, the ground substrate 24b is disposed between the first substrate 22 (analog substrate) and the component substrate 24a of the second substrate 24a (digital substrate).

Consequently, adverse effects due to the electrical characteristics of the digital control circuit of the component substrate 24a can be blocked by the around substrate 24b.

As a result, the electrical characteristics of the digital control circuit are less likely to have an adverse effect on the characteristics of the analog measurement circuit.

As shown in FIG. 5, the antenna substrate 27 in this embodiment is disposed so as to be perpendicular to the bottom surface of the main body case 20, but the inclination may be set so as to be oblique to the bottom surface, according to the shape of the main body case 20.

For example, when the shape of the main body case 20 is a truncated cone shape, the antenna substrate 27 is disposed along the inner peripheral surface of the main body case 20. Therefore, the antenna substrate 27 may be disposed in a state in which the upper portion of the antenna substrate 27 is inclined inward in the radial direction. In this case, the antenna substrate 27 may be formed in an elongated arc shape, and one end may be linked to the connector 23.

Again in this configuration, the long antenna unit 18 is disposed at a position that is away from other components containing metal (such as the measurement unit 12, the controller 13, the battery 14, and the communication unit 17), that is, along the inner peripheral surface 20aa. Therefore, there is no need to provide the first substrate 22 or the second substrate 24, on which other components containing metal are mounted, with an area where no components are mounted around the antenna unit 18.

This allows the base substrate 21 to be made smaller, and as a result, the size of the transmitter 7 can be reduced.

INDUSTRIAL APPLICABILITY

It is anticipated that the present invention will find use as a communication device that performs communication using an antenna unit.

REFERENCE SIGNS LIST 1 biological information measuring device
2 upper arm
3 sensor
4 skin tissue
5 base unit
6 sensor unit
7 transmitter (example of communication device)
8 adhesive portion
9 sensor unit mounting portion
10 fitting portion
11 connection terminal
12 measurement unit
13 controller
14 battery
15 temperature sensor
16 storage unit
17 communication unit
18 antenna unit
19 mobile telephone
20 main body case
20a upper case
20aa inner peripheral surface (inner wall surface)
20b lower case
21 base substrate
22 first substrate
23 connector
24 second substrate
24a component substrate
24b ground substrate
25 linking unit
26 ground
27 antenna substrate (third substrate)
27a extension (non-conducting portion)

The invention claimed is:

1. A communication device, comprising:
a main body case;
a controller that is provided inside the main body case;

a communication unit that is connected to the controller;

an elongated antenna unit that is connected to the communication unit, and a measurement unit that is connected to the controller and measures biological information, and a first substrate, a second substrate, and a third substrate that are disposed inside the main body case, the antenna unit is disposed on the third substrate along an inner wall surface of the main body case, the measurement unit is disposed on the first substrate disposed along a bottom surface of the main body case, and the controller is disposed on the second substrate disposed along the bottom surface of the main body case.

2. The communication device according to claim 1, wherein the controller is disposed at a position inside the main body case, away from the inner wall surface.

3. The communication device according to claim 1, further comprising a connector that links the first substrate and the second substrate, wherein the connector is linked to the third substrate on which the antenna unit is disposed.

4. The communication device according to claim 3, wherein the second substrate is disposed opposite the first substrate via the connector, and the third substrate is disposed on an outer peripheral portion of the first substrate and the second substrate.

5. The communication device according to claim 4, wherein, in a state in which the second substrate is disposed opposite the first substrate, the third substrate is disposed at a position corresponding to a gap between the second substrate and the first substrate.

6. The communication device according to claim 1, wherein the third substrate is disposed substantially parallel to the inner wall surface of the main body case.

7. The communication device according to claim 1, wherein the first substrate, the second substrate, and the third substrate are constituted by a single flexible substrate.

8. The communication device according to claim 1, wherein the antenna unit is formed by a conductive pattern, and a front and/or a back surface of the antenna unit is laminated with a resin substrate.

9. The communication device according to claim 1, wherein a battery that supplies power to the controller and the communication unit is disposed in the main body case, and the battery is disposed on an opposite side of the inner wall surface from the inner wall surface on which the antenna unit is disposed.

10. The communication device according to claim 9, further comprising a non-conducting portion that is provided on a distal end side of the antenna unit between the battery and the inner wall surface of the main body case.

11. The communication device according to claim 1, wherein the second substrate has a component substrate on which the controller is disposed, and a ground substrate on which a ground is disposed.

12. The communication device according to claim 11, wherein, in a state in which the second substrate is disposed opposite the first substrate, the ground substrate is disposed between the component substrate and the first substrate.

13. The communication device according to claim 1, wherein the main body case is formed in a dome shape.

* * * * *